(12) United States Patent
Lebkücher et al.

(10) Patent No.: US 7,736,514 B2
(45) Date of Patent: Jun. 15, 2010

(54) METHOD FOR EXTRACTING LACTIC ACID FROM AQUEOUS SUSPENSIONS

(75) Inventors: Helmut Lebkücher, Neustadt (DE);
Gernot Reiβenweber, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 353 days.

(21) Appl. No.: 11/995,997

(22) PCT Filed: Jul. 17, 2006

(86) PCT No.: PCT/EP2006/064324
§ 371 (c)(1),
(2), (4) Date: Jan. 17, 2008

(87) PCT Pub. No.: WO2007/009970
PCT Pub. Date: Jan. 25, 2007

(65) Prior Publication Data
US 2008/0230480 A1    Sep. 25, 2008

(30) Foreign Application Priority Data
Jul. 18, 2005   (DE) ................. 10 2005 033 432

(51) Int. Cl.
*B01D 11/00* (2006.01)
*C07C 59/08* (2006.01)

(52) U.S. Cl. .................. 210/634; 210/660; 562/589; 562/580; 426/425; 426/429; 426/431

(58) Field of Classification Search ............... 210/634, 210/660; 562/589, 580; 426/425, 429.431
See application file for complete search history.

(56) References Cited

U.S. PATENT DOCUMENTS

| 2,712,516 | A |  | 7/1955 | Kooi et al. | |
| 3,158,649 | A |  | 11/1964 | Colin et al. | |
| 6,872,314 | B2 | * | 3/2005 | Boyd et al. | 210/635 |
| 7,019,170 | B2 | * | 3/2006 | Eyal et al. | 562/589 |
| 7,144,977 | B2 | * | 12/2006 | Eyal et al. | 528/354 |
| 7,238,837 | B1 | * | 7/2007 | Eyal et al. | 562/589 |

FOREIGN PATENT DOCUMENTS

| DE | 1 268 088 | 5/1968 |
| DE | 32 22 837 | 12/1983 |
| EP | 0 159 585 | 10/1985 |
| EP | 0 184 789 | 6/1986 |

OTHER PUBLICATIONS

Chahal, S.P., "Lactic Acid", Ullmanns Encyclopedia of Industrial Chemistry, 2005, Wiley-VCH Verlag GmbH & Col. KGaA5. Aufl., Bd. A 15, 97-105, Weinheim, VCH.
Inskeep, Gordon C., et al., "Lactic Acid from Corn Sugar", Industrial and Engineering Chemistry, 1952, p. 1955-1966, vol. 44, No. 9.
English Translation of International Preliminary Report on Patentability, PCT/EP2006/064324, issued Jan. 28, 2008.

* cited by examiner

*Primary Examiner*—Ana M Fortuna
(74) *Attorney, Agent, or Firm*—Brinks Hofer Gilson & Lione

(57) ABSTRACT

The invention relates to a method for the continuous extraction of lactic acid from an aqueous suspension containing solids. According to said method, the aqueous suspension containing solids is brought into contact, in a counter-current, with an organic solvent that is partially miscible with water, in a column provided with filling agents which have a surface consisting of hydrophobic material, in such a way as to form an aqueous phase and an organic phase, such that the organic phase is guided as a dispersed phase in a section of the column comprising filling agents.

13 Claims, No Drawings

METHOD FOR EXTRACTING LACTIC ACID FROM AQUEOUS SUSPENSIONS

The present invention relates to a process for the continuous extraction of lactic acid from solids-comprising aqueous suspensions by bringing the suspensions into contact with organic solvents.

As is known, L(+)-lactic acid is prepared industrially by fermentational degradation of glucose-comprising raw materials (Ind. Eng. Chem. 44, 1958 (1952)).

The preparation of D(−)-lactic acid by means of suitable bacteria in a similar manner is also known (Ullmann's Encyclopedia of Industrial Chemistry, 5th edition, vol. A 15, 97-105, Weinheim, VCH). Here, the fermentation is carried out in the presence of calcium carbonate, so that the fermentation initially gives an aqueous solution or suspension which usually comprises from 6 to 20% by weight of calcium lactate. This solution or suspension is subsequently acidified with sulfuric acid, resulting in the calcium lactate being converted into free lactic acid and hydrated calcium sulfate being precipitated. The solids content, which consists mainly of hydrated calcium sulfate and bacteria, of the resulting suspension can be up to 10% by weight, based on the total weight of the suspension. This high solids content and in particular the biomass which is predominantly present in finely divided form and is difficult to separate off by mechanical means present great difficulties in the recovery of pure lactic acid from the acidic fermentation mixture.

The extremely complicated and costly removal of solids by filtration can be circumvented by the process for the extraction of the unfiltered, solids-comprising acidic fermentation broth which is described in EP-A-0 159 585. Here, the lactic acid is separated off by continuous extraction with an organic solvent by bringing the solids-comprising aqueous suspension obtained after fermentation and acidification into contact with the organic solvent in countercurrent in a column equipped with hydrophobic internals. According to EP-A-0 159 585, this is achieved particularly advantageously in pulsed sievetray columns and packed columns having ordered packing. Here, the aqueous suspension (i.e. the acidified fermentation broth) is fed into the upper part of the column and conveyed as disperse phase. The organic solvent is conveyed in countercurrent to the disperse aqueous phase. The lactic acid is recovered from the resulting solvent phase.

However, the extraction process of EP-A-0 159 585 cannot be implemented on an industrial scale since sievetray columns tend to become blocked after a few hours of operation because of the solids present. Although the process can be successfully carried out in a packed column, experiments carried out by the present applicant have shown that extraction yields in the order of only 72-75% of the lactic acid fed in are achieved here. This leads both to considerable yield losses and to a wastewater stream polluted with a large amount of organically bound carbon (TOC=total organic carbon).

It was therefore an object of the present invention to provide an industrially usable process for the continuous extraction of lactic acid from solids-comprising aqueous suspensions by bringing the suspensions into contact with organic solvents, which process makes a significant increase in the extraction yield possible and thus leads to a significant decrease in the TOC content of the wastewater stream obtained.

It has now surprisingly been found that this object is achieved by operating a packed column so that the organic phase is substantially conveyed as disperse phase.

The invention accordingly provides a process for the continuous extraction of lactic acid from a solids-comprising aqueous suspension, in which the solids-comprising aqueous suspension is brought into contact in countercurrent with an organic solvent which is not completely miscible with water to form an aqueous phase and an organic phase in a column provided with packing elements whose surfaces comprise hydrophobic material in such a way that the organic phase is conveyed as disperse phase at least in one section of the column comprising packing elements.

The process of the invention is basically suitable for the extraction both of D(−)-lactic acid and of L(+)-lactic acid and mixtures thereof from solids-comprising mixtures such as aqueous suspensions. According to the invention, use is made, in particular, of industrial aqueous lactic acid suspensions which are obtained in a manner known per se by acidification of an aqueous solution of calcium lactate prepared by fermentation with sulfuric acid (Ullmanns Enzyklopädie der technischen Chemie, 3rd edition, vol. 12, 525-537, Weinheim, Verlag Chemie). These suspensions comprise as solids particularly biomass from the fermentation and hydrated calcium sulfate ($CaSO_4.2\ H_2O$). Here and in the following, the term biomass refers to the bacteria together with residues of the nutrient medium used, e.g. yeasts. Suspensions of this type typically have a lactic acid content in the range from 5 to 15% by weight. The content of hydrated calcium sulfate is typically in the range from 5 to 10% by weight. The sulfuric acid content is usually in the range from 0.1 to 2% by weight. The biomass content is generally in the range from 0.01 to 5% by weight. In addition to the abovementioned components, the aqueous suspension consists essentially of water. Here, the expression "essentially" means that the proportion of further constituents other than the components mentioned above is generally less than 1% by weight, based on the total weight of the suspension.

According to the invention, organic solvents which do not mix completely with water under the extraction conditions, in particular at the temperatures employed, are used. The organic solvent which is not completely miscible with water is generally an aliphatic or cycloaliphatic, oxygen-comprising organic compound having at least 4, e.g. from 4 to 10, frequently from 4 to 8 and in particular from 4 to 6, carbon atoms. The solvents usually have no heteroatoms apart from oxygen. For example, the solvents can have one, two, three or four oxygen atoms per molecule.

Solvents which can be used according to the invention are, in particular, alkanols having at least 4, e.g. from 4 to 10, frequently from 4 to 8 and in particular from 4 to 6, carbon atoms, e.g. butanols such as 1-butanol, 2-butanol and isobutanol, pentanols such as 1-pentanol, 2-pentanol, 3-pentanol, 2-methyl-1-butanol, 2-methyl-2-butanol, 3-methyl-1-butanol, 3-methyl-2-butanol, 1,1-dimethylpropanol, 1,2-dimethylpropanol, 1-ethylpropanol, hexanols such as 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 1,1-dimethylbutanol, 1,2-dimethylbutanol, 1,3-dimethylbutanol, 2,2-dimethylbutanol, 2,3-dimethylbutanol, 2,4-dimethylbutanol, 3,3-dimethylbutanol, 2-ethylbutanol, 3-ethylbutanol, 1,1,2-trimethylpropanol, heptanols such as 1-heptanol, 2-heptanol, 3-heptanol, 4-heptanol, octanols such as 1-octanol, 2-octanol, 3-octanol, 4-octanol, 2-ethylhexanol, cyclic alkanols such as cyclopentanol and cyclohexanol each of which may optionally have one, two or three alkyl side chains each having from 1 to 3 and in particular 1 carbon atom(s), e.g. the cis and trans isomers of 2- and 3-methylcyclopentanol, 2-, 3- and 4-methylcyclohexanol and 3,3,5-trimethylcyclohexanol, ketones having at least 4, e.g. from 4 to 10, frequently from 4 to 8 and in particular from 4 to 6, carbon atoms, e.g. 2-butanone, 2-pentanone, 3-pentanone, 2-hexanone, 3-hexanone, cyclopentanone and cyclohexanone, ethers having at least 4, e.g. from 4 to 10, frequently from 4 to 8 and in particular from 4 to 6, carbon atoms, e.g. diethyl ether, di-n-propyl ether, diisopropyl ether, di-n-butyl ether, diisobutyl ether and methyl tert-butyl ether, esters having at least 4, e.g. from 4 to 10, frequently from 4 to 8 and in particular from 4 to 6, carbon atoms, e.g. n-butyl acetate, isobutyl acetate and pentyl acetate. Apart from the pure solvents, it is also possible to use solvent mixtures. Preference is given to using alkanols having from 4 to 8 and in particular from 4 to 6 carbon atoms, particularly preferably butanols and/or pentanols and very particularly preferably isobutanol. The organic solvent is advantageously used in the form of the solvent saturated with water.

The amount of solvent used can be from 0.1 to 10 times, in particular from 0.2 to 5 times and especially from 0.5 to 3 times, the weight of the aqueous suspension used. The optimal amount of solvent can readily be determined by a person skilled in the art by means of routine experiments.

In the process of the invention, the aqueous suspension is brought into contact with the solvent in countercurrent in a column equipped with packing elements. Packed columns are per se suitable in principle and known to those skilled in the art. The columns used usually have a round, frequently symmetrical and usually circular or elliptical diameter or cross section. In industrial plants, the diameter of the columns used can be, for example, in the range from 0.3 to 2 m, in particular in the range from 0.3 to 1.2 m and especially in the range from 0.4 to 0.8 m. Such columns used in industry can have, for example, a length in the range from 3 to 25 m and in particular in the range from 5 to 20 m. Naturally the column is arranged in an upright position.

The packing elements comprise a hydrophobic material or the packing elements are provided with a coating of a hydrophobic material. Suitable hydrophobic materials are, in particular, hydrophobic polymers which are substantially stable at the extraction temperatures employed. These include, for example, polyolefins and halogenated, in particular partially fluorinated or perfluorinated, organic polymers and especially chlorinated and/or fluorinated or perfluorinated polyalkenes. Suitable polyolefins are, for example, polyethylene (PE) and polypropylene (PP). Suitable chloroorganic polymers are, for example, polyvinyl chloride (PVC) and polyvinylidene chloride (PVDC). Examples of fluoroorganic polymers are homopolymers and copolymers of monoethylenically unsaturated fluorinated monomers such as chlorotrifluoroethylene, hexafluoroisobutylene, hexafluoropropylene, perfluorovinyl methyl ether, tetrafluoroethylene, vinyl fluoride and vinylidene fluoride, especially fluorinated thermoplastics such as poly(vinyl fluoride) (PVF), polyvinylidene fluoride (PVDF), poly(tetrafluoroethylene) (PTFE), poly(chlorotrifluoroethylene) (PCTFE), ethylene-tetrafluoroethylene copolymers (E/TFE), poly(tetrafluoroethylene-co-hexafluoropropylene) (FEP), poly(tetrafluoroethylene-co-perfluoroalkyl vinyl ether) (PFA/TFA, also referred to as perfluoroalkoxy copolymers), in which the alkyl group has, for example, from 1 to 4 carbon atoms, and fluoro elastomers such as hexafluoropropylene-vinylidene fluoride elastomer (CFM), vinylidene fluoride-hexafluoropropylene-tetrafluoroethylene copolymer, tetrafluoroethylene-propylene copolymer (TFE/P), polyfluorosilicones, polyfluoroalkoxyphosphazenes and vulcanization products of fluororubbers.

Hydrophobic materials based on fluorinated organic polymers have the advantage that they suppress adhesion of organic solids, e.g. biomass from the fermentation, even more strongly than other hydrophobic materials. For this reason, packing elements whose surfaces are formed by fluoroorganic polymers are used in a preferred embodiment. Particular preference is given to using packing elements which comprise or are coated with polytetrafluoroethylene (PTFE), polyvinylidene fluoride (PVDF) or poly(tetrafluoroethylene-co-perfluoromethyl vinyl ether), poly(tetrafluoroethylene-co-perfluoroethyl vinyl ether), poly(tetrafluoroethylene-co-perfluoropropyl vinyl ether), poly(tetrafluoroethylene-co-perfluorobutyl vinyl ether) (PFA/TFA) or a mixture thereof. In particular, it is possible to use packing elements of steel, glass or ceramic which have been coated with the abovementioned hydrophobic materials. The packing elements can also consist entirely of the hydrophobic material. Packing elements composed of plastic, for example polyethylene, polystyrene or polypropylene, whose surface has a fluoroorganic coating are also suitable.

The packing elements are advantageously packing elements which have a low dead volume and a perforated surface. Examples of packing elements which have a low dead volume and a perforated surface are, in particular, cylindrical types such as Pall rings, including modified Pall rings such as the Raflux type from Rauschert, Hiflow rings, Ralu rings from Raschig, also Super rings (from Raschig), and also spherical bodies having a perforated spherical surface, e.g. Hackettes®, Envi-Pac® bodies and the like. The dimensions of the packing elements, e.g. the average diameter or the average thickness or length, are generally in the range from 1 to 90 mm and in particular in the range from 5 to 40 mm. To carry out the process of the invention, particular preference is given to using, for example, Hiflow, Pall or Super rings having a diameter in the range from 20 to 40 mm. In general, the packing elements are present in the column in the form of a random bed. Ordered beds and/or packings made up of the packing elements are also suitable in principle.

To carry out the process of the invention, the solids-comprising aqueous suspension is generally fed continuously into the upper part of the column, in particular at the top of the column. The flow rate set here depends, inter alia, on the dimensions of the column used and on the extraction conditions, in particular the temperature. In general, the aqueous suspension will be fed in at a rate in the range from 5 t/(h·m$^2$) to 40 t/(h·m$^2$). The organic solvent which is not completely miscible with water is fed in in the lower part of the column, in particular at the bottom of the column. The solvent is preferably saturated with water before it is fed in. Here too, the flow rate set depends on the dimensions of the column used and the extraction conditions. In general, the organic solvent will be fed in at a rate in the range from 5 t/(h·m$^2$) to 40 t/(h·m$^2$). When this procedure is employed, a first upper region having a continuous organic phase is formed in the top of the extraction column and a further lower region in which water forms the continuous phase is formed under the extraction conditions. Due to the introduction of the organic solvent in the lower region of the column, this is dispersed in the continuous aqueous phase present there, migrates upward through the column as disperse phase and coalesces in the upper region of the column to form a continuous organic phase. The section of the column in which the disperse organic phase coalesces to form a continuous organic phase is also referred to as phase boundary. This phase boundary between the lower aqueous phase and the upper organic phase is set, according to the invention, so that the organic phase is conveyed as disperse phase in a section of the column comprising at least 50%, preferably at least 60% and particularly preferably at least 75%, of the total length of the column. For the purposes of the invention, a disperse phase is a phase which is present as a fine dispersion in another phase such as a continuous dispersion medium.

The boundary between the continuous aqueous phase and the continuous organic phase is preferably (phase boundary) formed at the same height as the fill height of the packing elements, above this height or only insignificantly below it, in each case based on the total fill height of the packing elements. In an industrial plant, the phase boundary can, for example, be formed in the region from 0 to 2 m above the fill height, in the region of the fill height itself, or in the region from 0 to 1 m below the fill height. The fill height itself is preferably selected so that the organic phase is conveyed as disperse phase in a region of the column comprising at least 75%, particularly preferably at least 85% and very particularly preferably at least 95%, of the packing elements. The organic phase is most preferably conveyed as disperse phase in the total region of the fill height of the packing elements so that the phase boundary is above the fill height. In general, the fill height of the packing elements will be chosen so that at least 50% by volume, in particular at least 65% by volume and especially at least 75% by volume, of the total volume of the column is filled with packing elements. Here and in the following, the term fill height comprises both the bed height and the packing height of packing elements present in a random or ordered bed or packing. The term bed height is thus used synonymously with the term fill height in the present context.

According to the invention, the aqueous phase introduced in the upper part of the column is thus conveyed firstly as disperse phase, i.e. as a fine dispersion in the organic phase. An inversion of continuous and disperse phase then occurs at the phase boundary. The column is flooded with the aqueous phase up to the phase boundary, so that the organic phase formed in the lower part of the column as a result of introduction of the solvent is conveyed as disperse phase in this region of the column. It has been found to be advantageous to set the phase boundary at about the bed height of the packing elements and to choose the bed height so that the aqueous phase after it has been introduced is firstly conveyed as disperse phase in a region above the bed height of the packing elements. This region is usually in the order of not many meters, e.g. in the range from about 0.5 to 5 m and in particular in the range from 1 to 3 m, in each case above the bed height or phase boundary.

The solids-free organic phase comprising the extracted lactic acid is taken off at the top of the column, advantageously above the point at which the solids-comprising aqueous suspension is fed in. The solids-free organic phase taken off generally comprises at least 5% by weight and in particular at least 10% by weight of lactic acid, based on the total weight of the organic phase taken off.

A solids-comprising aqueous phase can be taken off at the bottom of the column. This comprises as solids, in particular, biomass from the fermentation employed to prepare lactic acid and the hydrated calcium sulfate precipitated on acidification of the fermentation broth. The solids-comprising aqueous phase taken off preferably comprises less than 2.5% by weight, in particular less than 1.5% by weight and especially less than 1% by weight, based on the total weight of the solids-comprising aqueous phase obtained, of lactic acid. Here, the lactic acid content is determined enzymatically, as described, for example, in Ullmann's Encyclopedia of Industrial Chemistry, 5th edition, CD-ROM, Enzymes—Enzymes in Analysis and Medicine, 5.3.2 Organic Acids, Lactic Acid, VCH. Extraction yields of more than 90% and in particular at least 92% of the lactic acid introduced can be achieved by the extraction process of the invention.

The extraction can be operated batchwise and is preferably operated continuously. The extraction is generally carried out at temperatures in the range from 10 to 90° C., in particular in the range from 25 to 80° C. Carrying out the extraction process at elevated temperature has advantages, particularly when using alkanols as solvents.

For this reason, alkanols, particularly preferably butanols and/or pentanols and very particularly preferably isobutanol, are used as solvents in a preferred embodiment. This is advantageous from a number of points of view. Firstly, the partial water-solubility of the alcohol leads to reduced wetting of the hydrophobic packing elements and thus to reduced coagulation of the disperse phase on the surface of the packing elements. Secondly, the lactic acid is partly converted into the corresponding esters in the extraction column at elevated temperature. This is a desirable effect when, in particular, the extracted lactic acid is to be completely or substantially esterified. Owing to these advantages, a significant saving in distillation costs can be achieved overall.

It goes without saying that in the case of an esterification of the lactic acid carried out, if appropriate, after the extraction, in particular with the alkanols used as solvents, a content of excess sulfuric acid in the aqueous suspension employed is advantageous since this is partly extracted together with the lactic acid and serves as catalyst in the esterification. Complete reaction of the lactic acid which has not yet been esterified in the extraction step can be achieved in a known manner in a subsequent batchwise or continuous esterification stage. For this purpose, the organic phase obtained by means of the extraction, which comprises lactic acid and lactic esters, can be heated, for example, to temperatures in the range from 60 to 140° C. to convert the lactic acid into lactic esters, with the water formed in the reaction being distilled off, if appropriate under reduced pressure. The lactic esters obtained in pure form by distillation are valuable industrial intermediates. They can also be cleaved in a known manner to give lactic acid and alcohol again, so that highly pure lactic acid is obtained in this way.

EXAMPLE 1

According to the Invention

An aqueous solution of calcium lactate prepared by fermentation was brought to a pH in the range from 1.0 to 1.5 by means of sulfuric acid. The suspension, which had a content of 11% by weight of lactic acid and a solids content of 8% by weight, was heated to a temperature of 70° C. 2.5 t/h of this suspension were fed continuously into the top of a packed column (length: 18 m, diameter: 0.6 m, random bed of polypropylene Pall rings having a diameter of 30 mm, bed height: 15 m). At the same time, 3.1 t/h of isobutanol saturated with water were introduced in countercurrent into the bottom of the column. The isobutanol/water phase boundary was set at the height of the bed height of the packing elements. An inversion of continuous and disperse phase at the phase boundary was achieved in this way. The aqueous phase was initially conveyed as disperse phase (about 1 to 2 m). Up to the phase boundary, the column was flooded by the aqueous phase, so that the isobutanol phase introduced at the bottom of the column was conveyed as disperse phase in this lower region. The aqueous phase saturated with isobutanol, including the solids content of hydrated calcium sulfate and biomass, was taken off at the bottom of the column. The solids-free extract comprising lactic acid flowed out at the top of the column. This was available for work-up by distillation.

The aqueous phase obtained at the bottom of the column comprised from 0.5 to 1.0% by weight of lactic acid, based on the total weight of the aqueous phase obtained at the bottom of the column, determined by enzymatic determination. This corresponds to an extraction yield of from 92 to 96% of lactic acid, based on the lactic acid fed in. Similar results were achieved when using packing elements composed of polyvinylidene fluoride.

EXAMPLE 2

According to EP-A-0 159 585

The column described in example 1 above was operated at the same loading so that the isobutanol/water phase boundary was located in the bottom region of the column.

The aqueous phase to be extracted was thus conveyed essentially as disperse phase. As in example 1, the aqueous phase comprising hydrated calcium sulfate was taken off at the bottom of the column and the isobutanol phase was taken off at the top of the column.

The aqueous phase obtained at the bottom of the column comprised from 3.1 to 3.5% by weight of lactic acid, based on the total weight of the aqueous phase obtained at the bottom of the column, determined by enzymatic determination. This corresponds to an extraction yield of from 72 to 75% of lactic acid, based on the lactic acid fed in.

The invention claimed is:

1. A process for the extraction of lactic acid from a solids-comprising aqueous suspension, in which the solids-comprising aqueous suspension is brought into contact in countercurrent with an organic solvent which is not completely miscible with water to form an aqueous phase and an organic phase in a column provided with packing elements whose surfaces comprise hydrophobic material in such a way that the organic phase is conveyed as disperse phase at least in one section of the column comprising packing elements.

2. The process according to claim 1, wherein the fill height of the packing elements is selected so that at least 50% by volume of the total volume of the column is filled with packing elements.

3. The process according to claim 1, wherein the organic phase is conveyed as disperse phase in a section of the column which comprises at least 50% of the fill height of the packing elements.

4. The process according to claim 1, wherein the solids-comprising suspension is fed in continuously at the top of the column and the organic solvent which is not completely miscible with water is introduced at the bottom of the column.

5. The process according to claim 4, wherein a solids-free organic phase is taken off at the top of the column above the point at which the solids-comprising suspension is fed in and a solids-comprising aqueous phase is taken off at the bottom of the column.

6. The process according to claim 1, wherein a continuous organic phase is formed in the upper region of the column and a continuous aqueous phase is formed in the lower region of the column and the boundary between the continuous aqueous phase and the continuous organic phase is formed at the same height as the fill height of the packing elements, above this height or only insignificantly below it.

7. The process according to claim 1, wherein the solids-comprising aqueous suspension has been obtained by acidification of an aqueous solution of calcium lactate prepared by fermentation with sulfuric acid.

8. The process according to claim 1, wherein the organic solvent which is not completely miscible with water is an aliphatic or cycloaliphatic oxygen-comprising compound having at least 4 carbon atoms selected from among alkanols, ketones, ethers and esters or a mixture thereof.

9. The process according to claim 8, wherein an alkanol having at least 4 carbon atoms is used as organic solvent which is not completely miscible with water.

10. The process according to claim 9, wherein isobutanol is used as alkanol.

11. The process according to claim 9, wherein the organic phase obtained by means of the extraction, which comprises lactic acid and lactic esters, is heated to temperatures in the range from 60 to 140° C. to convert the lactic acid into lactic esters, with the water formed in the reaction being distilled off.

12. The process according to claim 1, wherein the extraction is carried out at temperatures in the range from 10 to 90° C.

13. The process according to claim 1, wherein a solids-comprising aqueous phase comprising less than 2.5% by weight, based on the total weight of the solids-comprising aqueous phase obtained, of lactic acid is obtained after the extraction.

* * * * *